United States Patent [19]

Tsuno et al.

[11] Patent Number: 4,807,597
[45] Date of Patent: Feb. 28, 1989

[54] FIBERSCOPE

[75] Inventors: Koichi Tsuno; Mitsuru Nishikawa; Kunio Awazu, all of Osaka, Japan

[73] Assignee: Sumitomo Electric Industries, Ltd., Osaka, Japan

[21] Appl. No.: 119,235

[22] Filed: Nov. 5, 1987

Related U.S. Application Data

[63] Continuation of Ser. No. 819,078, Jan. 14, 1986, abandoned.

[30] Foreign Application Priority Data

Jan. 14, 1985 [JP] Japan .............................. 60-3247[U]
Feb. 26, 1985 [JP] Japan ............................ 60-25423[U]
Feb. 26, 1985 [JP] Japan ............................ 60-25424[U]

[51] Int. Cl.⁴ ............................................... A61B 1/06
[52] U.S. Cl. ....................................................... 128/6
[58] Field of Search ........................................ 128/4–8, 128/303.1, 395–398; 350/96.25, 96.26, 319

[56] References Cited

U.S. PATENT DOCUMENTS

| | | | |
|---|---|---|---|
| 3,417,745 | 12/1968 | Sheldon | 128/6 |
| 3,809,072 | 5/1974 | Ersek et al. | 128/23 |
| 3,868,514 | 2/1975 | Israelsson | 350/96.26 |
| 4,217,891 | 8/1980 | Carson | 128/6 |
| 4,257,670 | 3/1981 | Legrand | 350/319 |
| 4,369,768 | 1/1983 | Vukovic | 128/6 |

Primary Examiner—Max Hindenburg
Attorney, Agent, or Firm—Sughrue, Mion, Zinn, Macpeak & Seas

[57] ABSTRACT

A fiberscope having a covering tube, an image fiber for transmitting picture images and equipped with an optical system at its tip end for focusing an image of an object to be observed, and light guides for transmitting light and placed along with said image fiber. The image fiber and the light guides are enclosed in said covering tube. A plastic body formed of substantially transparent material and convex shape is provided at front ends of the light guides. Liquid guide passages are also provided between an inner peripheral surface of the covering tube and outer peripheral surfaces of the image fiber and the light guides. Outlet ends of the light guides are arranged in positions substantially symmetrical with respect to an output end of the image fiber, and outlet ends of the liquid guide passages are arranged in positions substantially symmetrical with respect to the outlet end of the image fiber.

4 Claims, 14 Drawing Sheets

FIBERSCOPE

This is a continuation of application Ser. No. 819,078 filed Jan. 14, 1986 now abandoned.

BACKGROUND OF THE INVENTION

This invention relates to a fiberscope utilizable for optically observing or examining dark places such as the interiors of blood vessels and the heart.

There is a known fiberscope as means for opticaly observing the interiors of blood vessels and the heart, the fiberscope comprising, as shown in FIGS. 1 through 3, a plurality of light guides 9 for transmitting light beams from a light source 3 to a region 5 being observed (the interior of a blood vessel 7 in FIG. 2) through a flexible coating tube 1; an image transmitting fiber 11 equipped with an image focusing lens 19 at the tip thereof, and a liquid guide passage 15 for introducing a physiological saline solution from a syringe 13 and forming a transparent zone by temporarily removing the blood flowing in front of the light guides 9 and the image focusing lens 19 at the tip of the image fiber 11 in the region 5 being observed. In that case, it is needed to secure a physiological saline flush having a flow rate equivalent to that of blood at the tip of the coating tube 1 so as to form the above-described transparent physiological saline solution zone. The liquid guiding passage 15 is unnecessary when a zone without the presence of an opaque solution such as blood is optically probed.

Referring to FIGS. 4 through 7, the construction of the tip of a fiberscope equipped with a conventional liquid guide passage will be described. FIG. 6 is a vertical sectional view of the tip portion. FIG. 4 is a sectional view taken on line A-A' of FIG. 6. FIG. 5 is a sectional view taken on line B-B' of FIG. 6. FIG. 7 is a perspective view of the tip thereof. In those Figures, an image pick-up adaptor 23 for coupling the image focusing lens 19 and the tip of the image fiber 11 is adhesive-bonded and fixed to a recess (reference number 39 of FIG. 10) in a molded tip portion 21 wherein the tips of the light transmitting guides 9 are buried by the method described later. Moreover, the outer face of the molded tip portion 21 and the coating tube 1 are adhesive-bonded and fixed. The coating tube 1 is prepared from polyethylene or vinyl chloride plastics, etc. and about 2.8 mm and 2.2 mm in outer and inner diameters, respectively. The adhesion between the outer face of the molded tip portion 21 and the coating tube 1 is reinforced by filling a coating-tube bonding aperture 25 with an epoxy resin adhesive to deal with an impact at the time of flushing. As shown in FIG. 7, the flush flow 27 is thus formed. The molded tip portion 21 is, as shown in FIG. 6, also slightly positioned back by $\Delta L_1$ from the front face of the coating tube 1 in order to remove the blood from the front face of the image focusing lens 19 and the light guides 9 efficiently.

Referring to FIGS. 8 through 10, subsequently, the method of preparing the aforementioned molded tip portion 21 will be described. As shown in FIG. 8, a fluoroplastic molding die 31 with an aperture 2 mm in diameter and about 10 mm in depth is first prepared and a bundle 33 of plastic fibers for use as light transmitting guides 9 and a fluoroplastic dummy tube 35 for forming the recess (reference number 39 of FIG. 10) in the molded tip portion 21 are inserted into a throughhole 29. The gap between the throughhole 29 of the molding die 31 and the bundle of the plastic fibers 33 as well as the dummy tube 35 is filled with epoxy resin. The profile shown in FIG. 9 is obtained by grinding one end face and removing the molding die 31 from the molded piece 37 after it is hardened. The dummy tube 35 is then pulled out of the molded piece 37 and part of the tube 35 is cut out so that the molded tip portion 21 having the recess 39 may be formed as shown in FIG. 10. FIGS. 11a and 11b illustrate the construction of another conventional fiberscope comprising a molded tip portion 41 having a central aperture for inserting and fixing a pickup adaptor, liquid guide passages 15 on the left- and right-hand sides and a plurality of light guides 9 for transmitting light, the light guides being buried in an annular form.

The conventional fiberscopes having the construction illustrated in FIGS. 1 through 11 poses the following problems:

(1) The angle of view ($\alpha$ of FIG. 12) of a fiberscope is determined by the focal length of the image focusing lens and the outer diameter of the image fiber. Although the angle of view may exceed 100 degrees depending on the condition, it is normally about 70 degrees. However, since the angle of illumination ($\beta$ of FIG. 12), i.e., the maximum angle of opening of illumination is determined by NA (the Numerical Apertures) of the optical fiber as a light guide for transmitting light, it is relatively small when a lens is hardly usable in front of the light guides whose tips are distributed in an annular form as a bundle of optical fibers is used to form the light guides. The numerical apertures is determined by the refractive indices of the core and the clad and, in the case of a fiber for transmitting visible light such as a plastic fiber, its value is 0.6 at the greatest. Consequently, the angle of illumination $\beta$ is limited to about 50 degrees under liquid such as blood where the fiberscope is mainly intended for use. For that reason, observation is impossible within a region 43 where the angle of illumination $\beta$ is smaller than that of view $\alpha$, as shown in FIG. 12.

(2) On the other hand, because the edge of the tip of the conventional fiberscope is obviously sharp, as shown in FIG. 7, it may damage the inner wall of the blood vessel, ureter, etc.

(3) As the outlets of the light guides are one-sided relative to the axial position of the image fiber, there is caused deflection in the distribution of illumination within the visual field. The shortcoming becomes conspicuous particularly when the position of an object being observed is close to the fiberscope.

(4) As the outlet of the liquid guide passage for introducing a flush is one-sided relative to the axial position of the image fiber, there is caused deflection in the visual field by flushing.

SUMMARY OF THE INVENTION

In view of the above-described problems inherent in the prior art, it is an object of the present invention to provide a fiberscope offering an enlarged angle of illumination and thus a wide visual field with a blunt tip.

Another object of the present invention is to provide a fiberscope capable of providing uniform visual field resulted from flushing and providing uniform distribution of illumination.

In order to accomplish the above-described objects, the fiberscope according to the present invention comprises a coating tube enclosing an image fiber for transmitting picture images, the image fiber equipped with an optical system at the tip thereof for focusing the image of an object being observed, and light guides for transmitting light, the light guides being placed along with said image fiber. The front faces of the light guides are covered with a substantially transparent plastic body in a convex shape.

The substantially transparent plastic body in a convex shape on the front faces of the light guides for transmitting light have the effect of enlarging the angle of illumination derived from the light guides. Moreover, the tip of the fiberscope is made blunt because of the convex plastic body.

Further, the fiberscope according to the present invention comprises an image fiber for transmitting plastic picture images, light guides for transmitting light and liquid guide passages, a tube adapted to cover them. At the tip of the fiberscope, the outlets of the light guides are arranged in positions substantially symmetrical about the outlet of the image fiber, and the outlets of the liquid guide passages are arranged in positions substantially symmetrical about the outlet of the image fiber.

BRIEF DESCRIPTION OF THE DRAWINGS

In the drawings:
FIGS. 1-12 illustrate a conventional fiberscope;
FIG. 1 is a constructional view of the fiberscope system;
FIG. 2 is a perspective view of the tip of the fiberscope inserted in the region where an object being observed is present;
FIG. 3 is a sectional view of the part inserted into the blood vessel;
FIG. 4 is a sectional view taken on line A-A' of FIG. 6;
FIG. 5 is a sectional view taken on line B-B' of FIG. 6;
FIG. 6 is a vertical sectional view of the tip of the fiberscope;
FIG. 7 is a perspective view of the tip thereof;
FIGS. 8-10 illustrate the method of preparing the molded tip portion;
FIG. 11b is a cross-sectional view of the fiberscope shown in FIG. 11a;
FIG. 12 illustrates the relation between the angles of illumination and view at the tip of the conventional fiberscope.

DESCRIPTION OF THE PREFERRED EMBODIMENTS

Referring to FIGS. 13 through 22, various embodiments of the present invention will be described.

Figure 13:
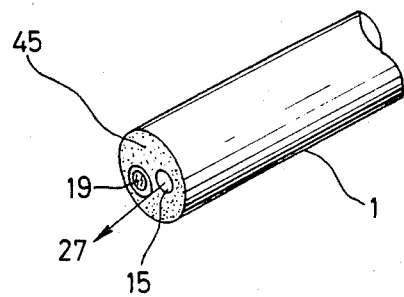
FIG. 13 is a perspective view of one embodiment of the present invention illustrating the tip of a fiberscope equipped with a liquid guiding passage.

FIG. 13 is a perspective view of the tip of a fiberscope with a liquid guide passage. A drop of substantially transparent resin is hardened on the front faces of light guides for transmitting light, except those of an image focusing lens 19 and a liquid guide passage 15, and the former is covered with a substantially transparent plastic body 45 in a convex shape extending up to the periphery of the tip of a coating for covering tube 1. As for the resin, use can be made of epoxy resin, ultraviolet-curing silicon, acrylic plastics, urethane resin, etc.

Figure 14:
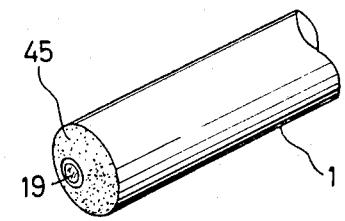
FIG. 14 is a perspective view of another embodiment of the present invention in the form of a fiberscope without the liquid guiding passage.

FIG. 14 is a perspective view of a fiberscope without a liquid guide passage, wherein a drop of substantially transparent resin is hardened on the faces of light guides for transmitting light, except that of the image focusing lens 19, and the former is covered with the substantially transparent plastic body 45 extending up to the periphery of the tip of the coated tube 1.

Figure 12:
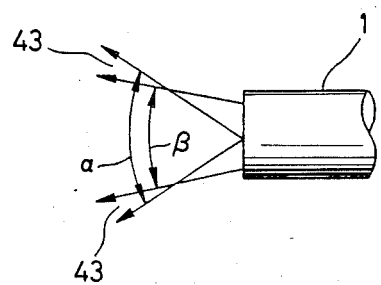
Figure 15:
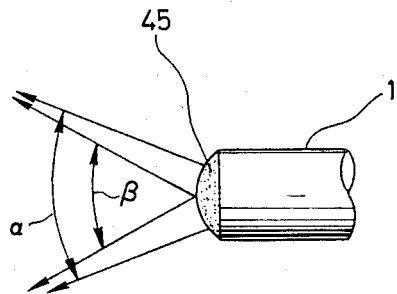
FIG. 15 illustrates the relation between the angles of illumination and view at the tip of the fiberscope according to the present invention.

As is obvious from FIGS. 13 and 14, if the front faces of light guides for transmitting light beams are covered with the substantially transparent convex plastic body 45, the angle of illumination β will become greater, as shown in FIG. 15, than that without such a plastic body (FIG. 12) and it will permit an increased range of observation. As shown in FIGS. 13 and 14, the fiberscope with a blunt edge may not damage the soft tissue of the blood vessel, ureter, etc. The magnification of the angle of illumination $\beta$ and the rounding of the tip can be attained as in the cases of FIGS. 13 and 14 even if the substantially transparent convex plastic body is not completely extended up to the periphery of the tip of the coating tube 1, for instance, only the front faces of light guides for transmitting light beams are thus covered.

Figure 1:
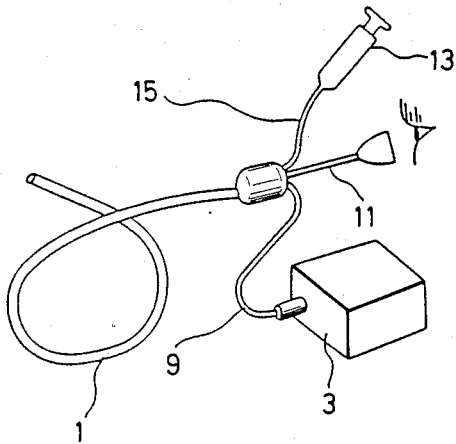
Figure 2:
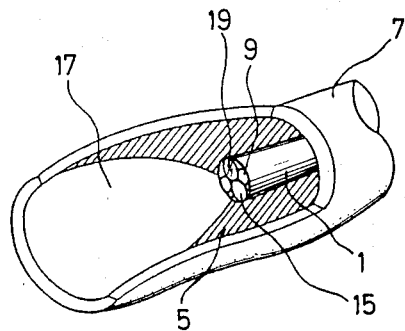
Figure 3:
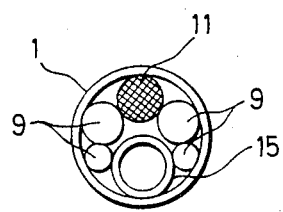
Figure 4:
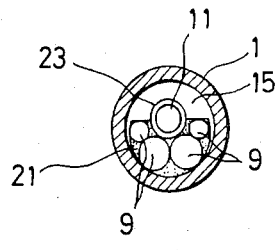
Figure 5:
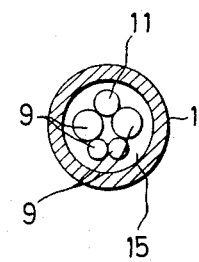
Figure 6:
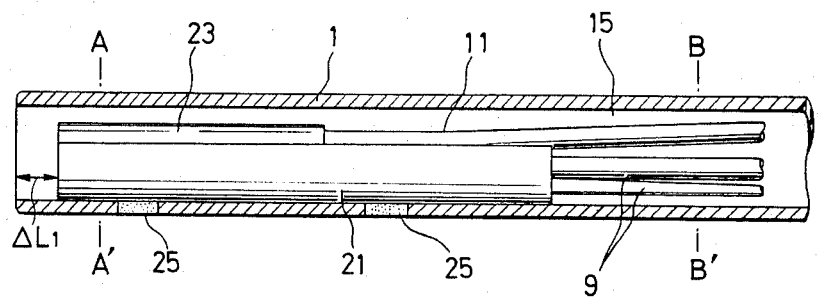
Figure 7:
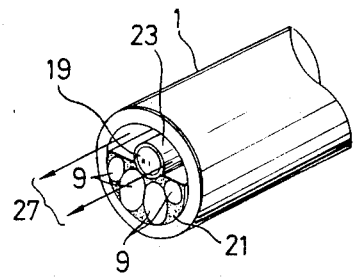
Figure 8:
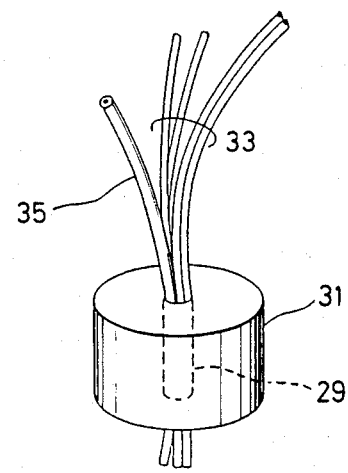
Figure 9:
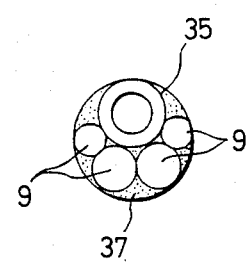
Figure 10:
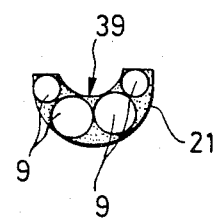
Figure 11A:
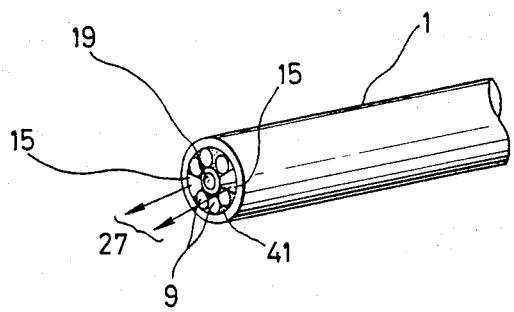
FIG. 11a is a perspective view of the tip of another conventional fiberscope.
Figure 11B:
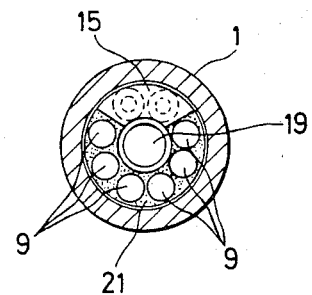

Subsequently referring to FIGS. 16 through 19, the method of forming the substantially transparent convex plastic body will be described by taking the case of applying the present invention to the conventional fiberscope equipped with a liquid guide passage shown in FIG. 11.

Figure 16:
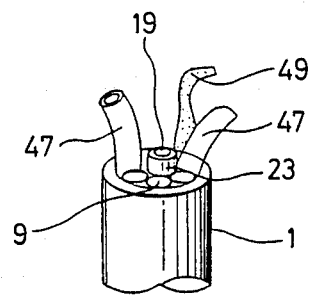
FIGS. 16-19 illustrate the method of preparing the substantially transparent convex plastic body according to the present invention.
Figure 17:
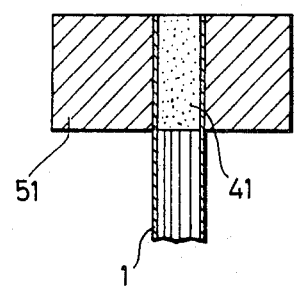
Figure 18:
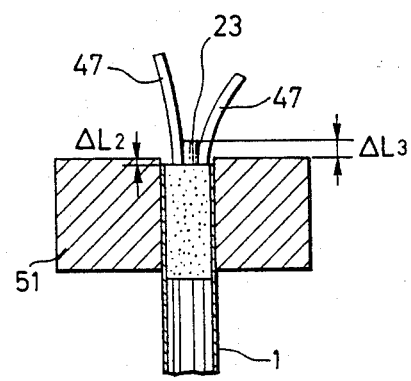
Figure 19:
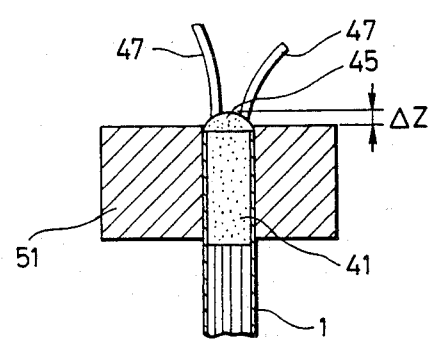

In reference to FIG. 16, such a method roughly comprises protruding the pick-up adaptor 23 from the molded tip portion to a suitable extent, adhesion-bonding the adaptor 23 thereto to prevent the plastics from attaching to the image focusing lens 19, inserting a dummy tube 47 of fluoroplastics to prevent the liquid guide passage for the flush flow from being clogged with the plastics and dropping substantially transparent suitable plastics 49 from upside to the tip portion. Since the plastics has suitable viscosity, there is formed a convex swell in proportion to the periphery of the pick-up adaptor 23 and the side of the dummy tube 47. The surface of the convex plastic is smooth because of the surface tension of the plastics. Accordingly, the front face of the fiberscope excluding the image focusing lens 19 and the liquid guide passage for the flush flow is covered with a smooth substantially transparent convex plastic body by pulling out the dummy tube 47 after the resin is hardened. It is suggested to drop the plastics by the following method, which comprises inserting the tip of the fiberscope into a mold 51 of fluoroplastics and buffing the front face thereof (excluding the pick-up adaptor) as shown in FIG. 17, lowering the tip by about $\Delta L_2 = 0.2$ mm from the plastic molding die 51, protruding the pick-up adaptor 23 by $\Delta L_3 = 0.3$ mm, inserting the dummy tube 47 into the adaptor 23 and dropping the substantially transparent plastics 49 while the tip of the fiberscope is being inserted into the plastic molding die 51 as shown in FIG. 19. The buffing acts to improve the adhesion between the plastics 49 and the molded tip portion 41 while reducing the light transmission loss. By lowering the tip of the fiberscope by $\Delta L_2$, the plastics is prevented from flowing out of the edge and the connection between the periphery of the coating tube 1 and the convex plastic body 45 is considerably smoothed. Moreover, the protrusion of the pick-up adaptor 23 by $\Delta L_3$ allows the adjustment of the quantity $\Delta Z$ of the protrusion of the convex plastic body 45.

Figure 20:
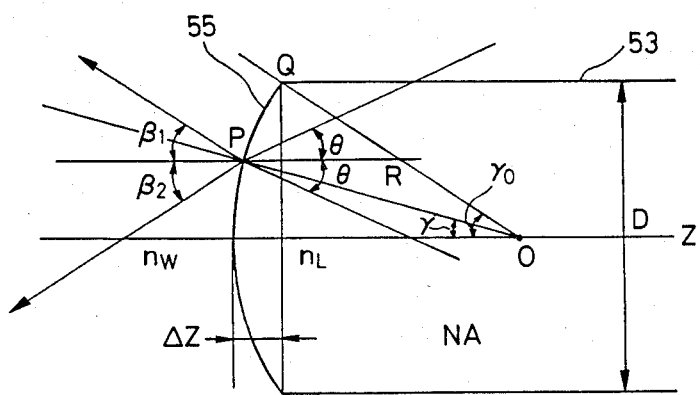
FIGS. 20 and 21 illustrate a basis for enlarging the angle of illumination.
Figure 21:
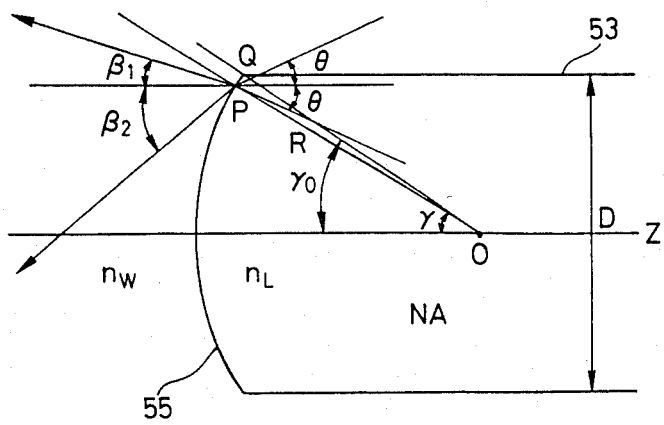
Figure 22:
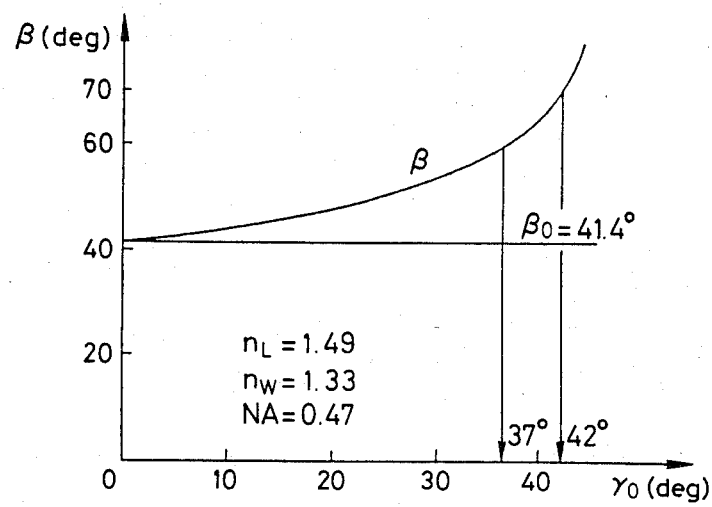
FIG. 22 is a graph representing the related equations.

Referring to FIGS. 20 through 22, the relation between the quantity $\Delta Z$ of the protrusion of the convex plastic body 45 and the angle $\beta$ of illumination will be described. In FIGS. 20 and 21, given the diameter D; refractive index nL; number of apertures NA of the group of light guides 53 having a convex 55 at their tips; the curvature radius R of the convex; the quantity $\Delta Z$ of the protrusion of the convex; the optic axis Z; the angle $\gamma_0$ between line OQ connecting the center O and a point Q on the periphery of the convex, and the optic axis Z; the angle $\gamma$ between line OP connecting a point P on the convex and the center), and the optic axis Z; $\theta = \sin^{-1}$ (NA/nL); the refractive index nW of the external portion (such as water); and the angles $\beta_1$, $\beta_2$ between the radiated light and the optic axis when the light at an angle of $\theta$ to the optic axis is refracted by the convex and radiated, (i) when $0 \leq \gamma < \theta$ shown in FIG. 20, since $$nW\sin(\beta_1 - \gamma) = nL\sin(\theta - \gamma)$$

$$nW\sin(\beta_1 + \gamma) = nL\sin(\theta + \gamma)$$

$$\beta_1 = \sin^{-1}\{(nL/nW)\sin(\theta-\gamma)\} + \gamma \quad (1)$$

$$\beta_2 = \sin^{-1}\{(nL/nW)\sin(\theta-\gamma)\} - \gamma \quad (2)$$

(ii) when $\theta < \gamma \leq \gamma_0$ shown in FIG. 21, since $$nW\sin(\gamma - \beta_1) = nL\sin(\gamma - \theta)$$

$$nW\sin(\beta_2 + \gamma) = nL\sin(\theta + \gamma)$$

$$\beta_1 = \gamma - \sin-1\{(nL/nW)\sin(\gamma-\theta)\} \quad (3)$$

$$\beta_2 = \sin^{-1}\{(nL/nW)\sin(\theta+\gamma)\} - \gamma \quad (4)$$

$\beta_1 < \beta_2$ from the equations (1)-(4) and, as the maximum value of $\beta_2$ is considered:
$\beta_2 = \sin^{-1}\{(nL/nW)\sin(\theta+\gamma_0)\} - \gamma_0$, the angle of illumination $\beta$ is given by $$\beta = 2\sin^{-1}[(nL/nW)\sin\{\sin^{-1}(NA/nL)+\gamma_0\}] - 2\gamma_0 \quad (5)$$

when $\theta = \sin^{-1}(NA/nL)$ is taken into consideration. However, since $\gamma_0 = \sin(D/2R)$ and $\Delta Z = R(1-\cos\gamma_0)$, the required quantity $\Delta Z$ of protrusion will be obtained from nL, nW, NA and D if the desired angle of illumination $\beta$ is determined.

Given $nL = 1.49$, $nW = 1.33$ and $NA = 0.47$ as in a general case, the equation (5) will be represented by a graph of FIG. 22.

(1) Accordingly, assuming $\beta = 60°$ and $D = 1.7$ mm as $\gamma_0 = 37°$, $R = 1.7/2\sin 37° = 1.4$ mm
Therefore,
$\Delta Z = 1.4(1 - \cos 37°) = 0.28$ mm.

(2) Assuming $\beta = 70°$ and $D = 1.7$ mm as $\gamma_0 = 42°$, $R = 1.7/2\sin 42° = 1.3$ mm
Therefore, $\Delta Z = 1.3(1 - \cos 42°) = 0.33$ mm According to the above-described embodiments of the present invention, the front faces of light guides for transmitting light are covered with a substantially transparent convex plastic body so that the enlarged angle of illumination can widen the visual field of a fiberscope. The presence of the convex plastic body, moreover, makes the tip of the fiberscope blunt and may least damage an object being observed. As the convex plastic body can simply be obtained by dropping substantially transparent resin and hardening it, production cost is reducible compared with the use of a lens. When plastic fibers are used as the light guides for transmitting light, the convex plastic body protects their end faces. The intensity of illumination upon the object being observed becomes uniform because of the convex plastic body.

Still another embodiment will be described with reference to FIGS. 23(a)-23(c).

Figure 23A:
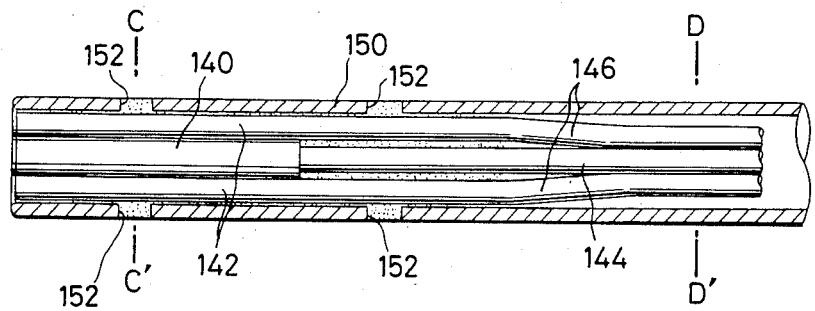
FIG. 23(a) is a vertical sectional view of still another embodiment of the present invention.
Figure 23B:
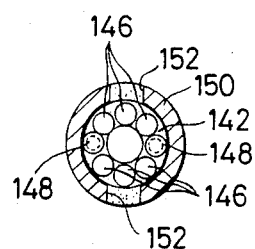
FIG. 23(b) is a sectional view taken on line C-C' of FIG. 23(a)
Figure 23C:
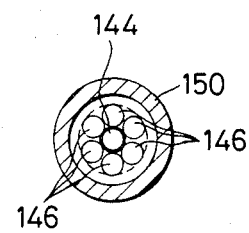
FIG. 23(c) is a sectional view taken on line D-D' of FIG. 23(a)

FIG. 23(a) is a vertical sectional view illustrating an embodiment of the present invention. FIG. 23(b) is a sectional view taken on line C-C'. FIG. 23(c) is a sectional view taken on line D-D'. As shown in those figures, a pickup adaptor 140 is inserted in the center of a molded tip portion 142 and adhesive-bonded thereto, and the front end face of the pick-up adaptor 140 is equipped with an image focusing lens, whereas an image fiber 144 is coupled to the base face thereof. Consequently, the pick-up adaptor 140 in this example forms the outlet of the image fiber 144. Six light guides 146 are buried in the molded tip portion 142 and a pair of three light guides 146 are arranged symmetrically about the pick-up adaptor 140. Moreover, a pair of liquid guide passages 148 are formed in the molded tip portion 142 symmetrically about the pick-up adaptor 140. The molded tip portion 142 is adhesive-bonded to a coating tube 150 and four tube-bonding apertures 152 formed in the coating tube 150 are filled with the adhesive so that the coating tube 150 may withstand an impact at the time of flushing. The diameters of the light guide 146 and the liquid guide passage 148 are 0.5 mm and 0.6 mm, respectively.

In the above-described embodiment, the distribution of illumination and the visual field resulted from flushing are made uniform since the light guides 146 and the liquid guide passages are arranged symmetrically about the pick-up adaptor 140.

Figure 24:
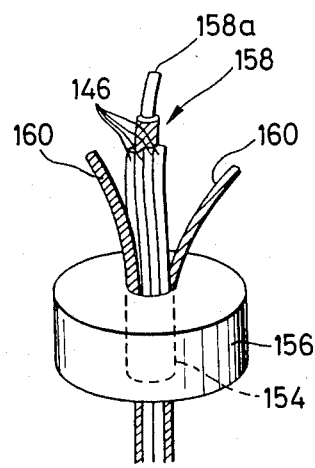
FIG. 24 illustrates the method of making the molded tip portion of the image fiber of FIG. 23.

Subsequently, referring to FIG. 24, the method of making the molded tip portion 142 will be described. A molding die 156 with a throughhole 154 is first prepared and a dummy tube 158 for the image fiber, the light guides 146 and a dummy tube 160 for the liquid guide passages are inserted into the throughhole 154. In that case, the light guides 146 and the dummy tube 160 for the liquid guide passages are arranged symmetrically about the dummy tube 158 for the image fiber. The throughhole 154 is filled with epoxy resin while the arrangement above is held. After the epoxy resin is hardened, the dummy tube 158 is pulled out to form a hole for inserting the pick-up adaptor, whereas the dummy tube 160 is pulled out to form the liquid guide passages 148. There is thus made the molded tip portion 142 wherein the light guides 146 and the liquid guide passages 148 are arranged symmetrically. A metal core 158a is inserted into the dummy tube 158 to prevent it from deforming. On the other hand, the dummy tube 160 is hollow so that its shape can be changed in accordance with the arrangement of elements. Since the hole for inserting the pick-up adaptor and the liquid guide passages 148 are formed only by pulling out the dummy tubes 158,160, the fiberscope can readily be processed.

Figure 25:
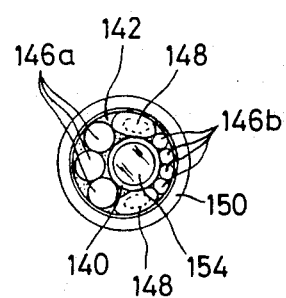
FIG. 25 is a front view of still another embodiment of the present invention.

FIG. 25 illustrates still another embodiment of the present invention, wherein two liquid guide passages 148 are arranged in positions substantially symmetrical about a pickup adaptor 140. Moreover, three light guides 146a each having 0.5 mm in diameter are provided on the left-hand side of the pick-up adaptor 140, whereas four light guides 146b each having 0.25 mm in diameter are installed on the left-hand side thereof. Consequently, the light guides 146a, 146b are substantially symmetrical. Reference number 154 indicates an image focusing lens.

As set forth above, the outlets of light guides and those of liquid guide passages are arranged in positions substantially symmetrical with respect to the outlet of the image fiber. Accordingly, the distribution of illumination within the visual field is made uniform and the visual field secured by flushing offers least deflection.

Figure 26:
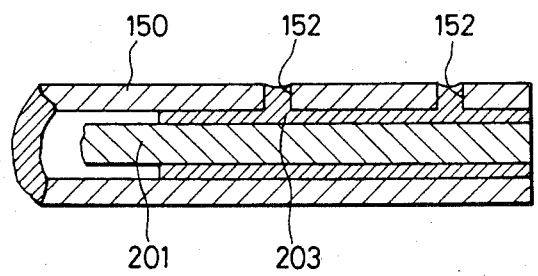
FIG. 26 is a sectional view of the end construction of an optical fiber sensor.

Further, in the present invention an additional improvement is made at the end portion of the fiberscope in terms of bonding between the protective tube 150 and optical fiber bundle accommodating therein a plurality of optical fiber elements. The improvement will be described with reference to FIGS. 26-28. FIG. 26 shows an optical fiber sensor for use in an endoscope. More specifically, FIG. 26 shows the tip construction of an optical fiber sensor, i.e., a bundle of optical fibers in an endoscope and a tube formed of synthetic resin such as polyethylene or fluorine plastics for enclosing the former.

The construction of an optical fiber sensor in an endoscope is such that a bundle of optical fibers incorporating a number of optical fiber elements constituting image elements is enclosed in a tube of synthetic resin such as polyethylene and fluorine plastics fit for medical use. Since such an optical fiber sensor is inserted into the blood vessel and the body, its construction must particularly be stable and fully reliable for a long period of use.

FIG. 26 illustrates an example of the tip construction of a bundle of optical fibers. In FIG. 26 and in the abovedescribed embodiments, a bundle 201 of optical fibers of an optical fiber sensor is bonded to a medical tube 150 of polyethylene and fluorine plastics with an epoxy resin adhesive 203 applied between the bundle 201 of optical fibers and the tube 150 because there is no fully suitable adhesive capable of sticking on polyethylene and fluorine plastics, whereas part of the adhesive 203 is forced to communicate with a plurality of holes 152 provided in the tube 150 so as to fill the holes 152 with the adhesive and reinforce the adhesion between the tube 150 and the adhesive 203 mechanically.

While an optical fiber sensor is used for a long time, the tube 150 may come off the bundle of optical fibers, or the tube 150 may be gradually deteriorated or torn because the stress is concentrated at the holes 152. Damage may also expand because of temperature changes. As a result, stepped clearance may be generated between the end faces of the bundle of optical fibers and the tube. Consequently, an unexpected trouble may occur, that is, a thrombus may crop up around the stepped portion when the optical fiber sensor is used in the blood vessel.

The present invention is intended to remedy the shortcomings mentioned above and to provide the end construction of an optical fiber sensor not only highly reliable but also free from damage and deformation despite long range use by solidly coupling the ends of a bundle of optical fibers and a plastic tube enclosing the bundle of optical fibers. The end construction of the optical fiber sensor that has accomplished the above-described object is such that the gap between an outer periphery of end portion of a bundle of optical fibers and an inner periphery of an end portion of the plastic tube enclosing the bundle of optical fibers is filled with an adhesive so that the ends of the tube and the bundle of optical fibers can solidly be fixed. The inner peripheral surface of the end portion of the tube is formed with a plurality of circumferential grooves, so that tight connection with respect to the bundle is obtainable.

Figure 27:
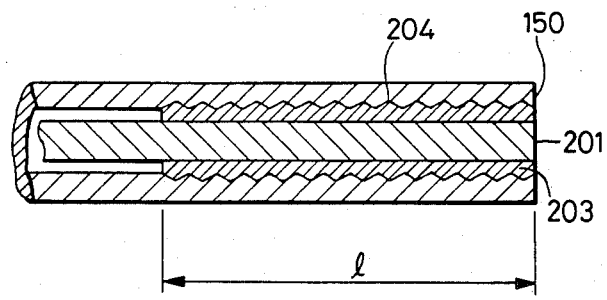
FIG. 27 is a sectional view of the end construction of one embodiment of the present invention.

FIG. 27 is a sectional view of the end portion of an optical fiber sensor embodying the present invention. The gap extends over a length of l from the tip. The gap is provided between a bundle 201 of optical fibers and a tube 150 of synthetic resin such as polyethylene or fluorine plastics accompanying relatively less bioreaction when medically used to enclose the optical fibers 1. The gap is filled with an adhesive, for instance, epoxy resin 203 so that the end portions of the bundle of optical fibers and the tube may be fixed. The adhesive epoxy resin used to fill the gap between the tube 150 and the bundle 201 of optical fibers generally ensures firm adhesion with respect to the bundle 201 coated with epoxy resin or similar materials. However, because the adhesion between polyethylene or fluorine plastics and the adhesive is bad, there are provided many grooves 204 cut in the circumferential direction of the inner face of the tube 150, and the epoxy resin adhesive 203 used to fill the gap between the tube 150 and the bundle of optical fibers is also used to fill the grooves 204. Accordingly, the bundle 201 of optical fibers is mechanically stuck on the tube 150 with the adhesive 203, thus firmly engaging with the tube 150 in the axial direction. When the tube 150 is prepared from polyethylene, for instance, and the gap is filled with an epoxy resin adhesive between the bundle and the polyethylene tube 150 having a thread ridge diameter of 1.4 mm and axial length of the threaded portion l=3 mm, tensile strength of more than 3 kg was obtained.

Figure 28:
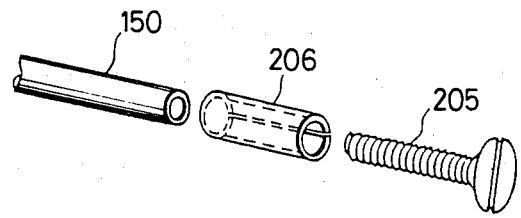
FIG. 28 illustrates the procedure for making the embodiment shown in FIG. 27.

Subsequently, an example of the method of making the end portion of the optical fiber sensor thus constructed according to the present invention will be described. As shown in FIG. 28, (1) a screw 205 or a tap having an outer diameter slightly greater than the inner diameter of the polyethylene tube 150 is, for instance, thrusted by a depth of l into the end of the tube 150;

(2) the end of the tube 150 with the screw 205 thrusted therein is covered with an elastic thin-wall stainless pipe 206 having an inner diameter roughly equal to the outer diameter of the tube 150 within the range of l, the pipe being provided with a longitudinal slot;

(3) the combination of the tube 150, the screw 205 and the longitudinally slotted pipe 206 is dipped into hot water having softening temperature of the plastic tube 2 (90° C. in the case of polyethylene) so that the tube 150 may be thrusted into the grooves of the screw 205 as it is subjected to plastic deformation because of the restoring force of the longitudinally slotted pipe 206;

(4) subsequently, the screw 205 is removed from the tube 150;

(5) grooves are formed in the inner face of the tube 150 over the length of l from the end thereof by removing the longitudinally slotted pipe 206 from the tube 150. The procedures 4 and 5 may be implemented reversely; and (6) the bundle 201 of optical fibers is inserted into the tube 150, and the end faces of the bundle of optical fibers and the tube 150 are flush with each other, whereas the gap between the tube and the bundle of optical fibers is filled with epoxy resin 203, which is then hardened.

The end portions of the bundle of optical fibers and the tube 150 enclosing the former are thus firmly joined over the length of l and there has been made available the end construction of an optical fiber sensor usable with greater reliability for a long period of time.

In the end construction of the optical fiber sensor according to the present invention, a number of grooves are cut in the circumferential direction of the inner face of the tube enclosing the bundle of optical fibers. Space defined between the tube and the bundle is filled with a resin adhesive over the desired length from the end of the bundle of optical fibers of the optical fiber sensor, and the grooves cut in the circumferential direction act as locking, thus making it possible to obtain high bonding strength in the axial direction. Moreover, there have been eliminated the troubles caused by the generation of a recess in the end faces of the bundle of optical fibers and the tube. Further, increase of outer diameter at the joined ends can be prevented, which has resulted in superior effect on the use of small diameter endoscopes. The end construction of an optical fiber sensor according to the present invention can effectively be applicable to not only endoscopes for medical use but also to various optical fiber sensors for industrial use.

Next, explanation will be made on the image fiber according to the present invention, which is used in combination with a lens. That is, the embodiments hereinbelow concerns an improvement of the image pickup optical system which is an objective optical system which is applied to a medical or industrial endoscope, especially to a small diameter endoscope.

Figure 29:
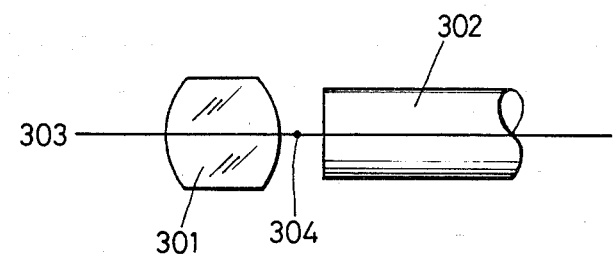
FIG. 29 is an explanatory diagram showing one example of an image pickup optical system for small diameter endoscopes which has no lens iris.

A small diameter endoscope of this type uses a lens 301 and an image fiber 302 as shown in FIG. 29. The endoscope is used for instance in the case where the object side is water 303, and the image side is air 304.

It is assumed that, in FIG. 29, the lens 301 has a front side curvature radius of 0.36 mm, a rear side curvature radius of 0.47 mm, an outside diameter of 0.66 mm, a length of 0.76 mm, and a refractive index of 1.85. If, when the lens is focused on a point at a distance of 10 mm in the water which is the object side as was described above, calculation is made to detect convergent spot sizes at six points, 5(1) through 5(6), in the range of a half view angle 21° (half of the angle of view) as shown in a field depth calculation diagram of FIG. 31, then as a result of the optical tracing operation with a computer 42 $\mu$m, 52 $\mu$m, 41 $\mu$m, 49 $\mu$m, 45 $\mu$m and 41 $\mu$m are obtained as spot size radii, respectively. And the image element distance of the image fiber is 5 to 10 $\mu$m. Therefore, the formed image is foggy.

Therefore, the present embodiment should provide an image pickup optical system high in resolving power in which the above-described difficulty has been eliminated. For this purpose, a lens iris (305 in FIG. 30) having a suitable size is formed on the front surface of an image pickup optical system according to a simple method.

Figure 30:
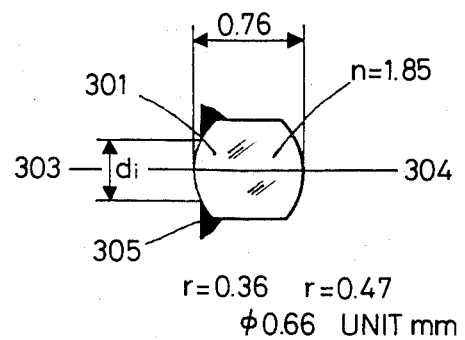
FIG. 30 is an explanatory diagram showing one example of an image pickup optical system with a lens iris according to this invention.

By applying the aforementioned lens iris 305 to the image pickup optical system as shown in FIG. 30, the resolving power is increased, and the depth of field in the range of observation is also increased.

As shown in FIG. 30, the same lens 301 as that in FIG. 29 and a lens stop 305 having an aperture diameter di are used. In this case, if the aperture diameter is set to 0.6 mm, 0.5 mm and 0.4 mm, then the spot size radius is decreased. For instance when the aperture diameter di is set to 0.4 mm, the spot size radii at the aforementioned points 5(1) through 5(6) (the angle of view being 60°) are 5 $\mu$m, 18 $\mu$m, 7 $\mu$m, 28 $\mu$m, 20 $\mu$m and 32 $\mu$m, respectively.

Figure 31:
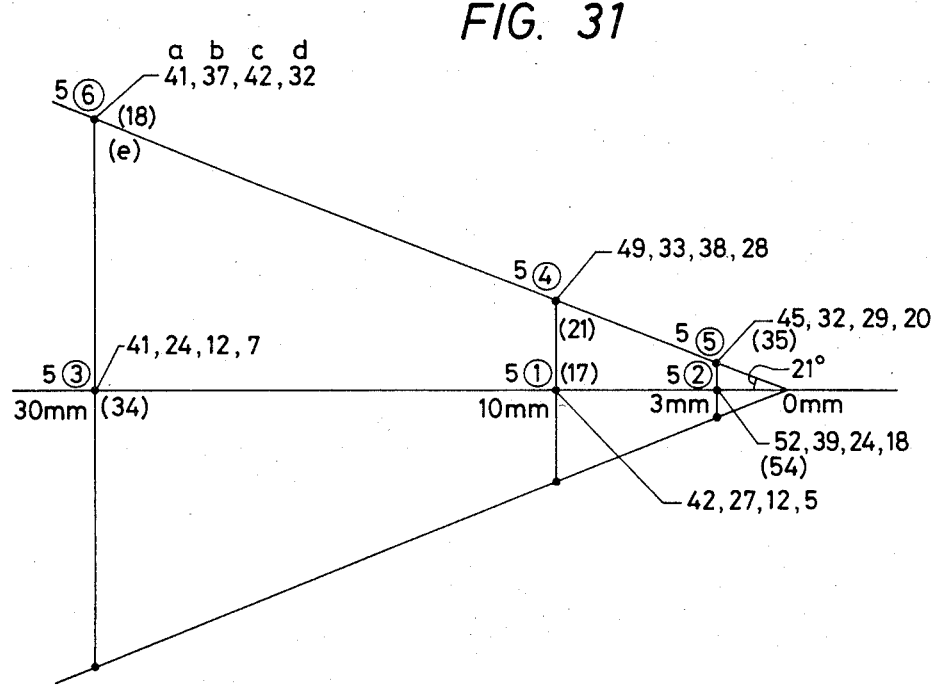
FIG. 31 is a diagram indicating the effects which are provided when a lens iris is applied to an image pickup optical device comprising one lens.

In FIG. 31, a to (e) show spot size radius (SP) whose unit is $\mu$m. a is SP at the front of lens having no iris and aperture diameter is 0.66 mm. Focus point is adjusted at the position 1 . b is SP at aperture diameter of 0.60 mm . c is SP at aperture diameter of 0.50 mm. d is SP at aperture diameter of 0.40 mm. (e) is SP similar to the condition of a but iris is provided to provide aperture diameter of 0.40 mm. In these cases, view angle is 41° and diameter of image fiber is 0.47 mm. By providing a stop having aperture diameter of 0.40 mm, spot size will be improved by 12 to 35% at the axis, and by 44 to 78% at the area surrounding the axis.

Figure 32:
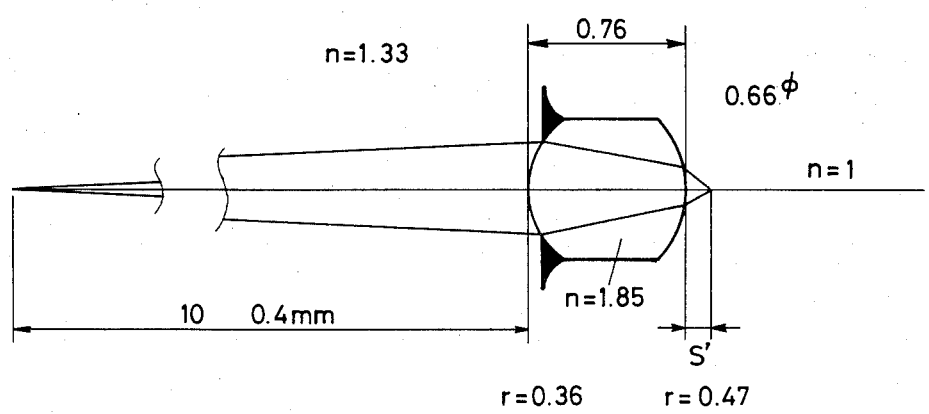
FIG. 32 is an explanatory diagram showing the optical system according to the invention which is focused on an object at a distance of 10 mm (in the water)
Figure 33:
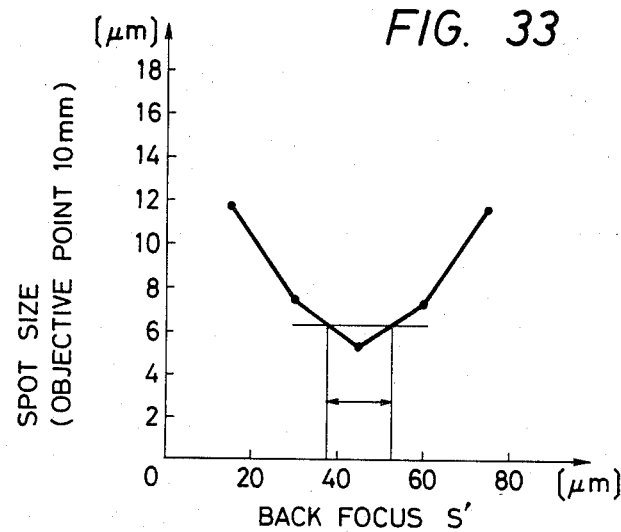
FIG. 33 is a graphical representation indicating a calculation of the depth of focus in the case of FIG. 32.

As shown in FIGS. 32 and 33, the depth of focus is about 15 μm, and the lens should be focused in this range.

In FIG. 33, the region (depth of focus) at which the spot size does not exceed 1 μm from the spot size at best focus is about 15 μm (within a range shown by an arrow).

Figure 34:
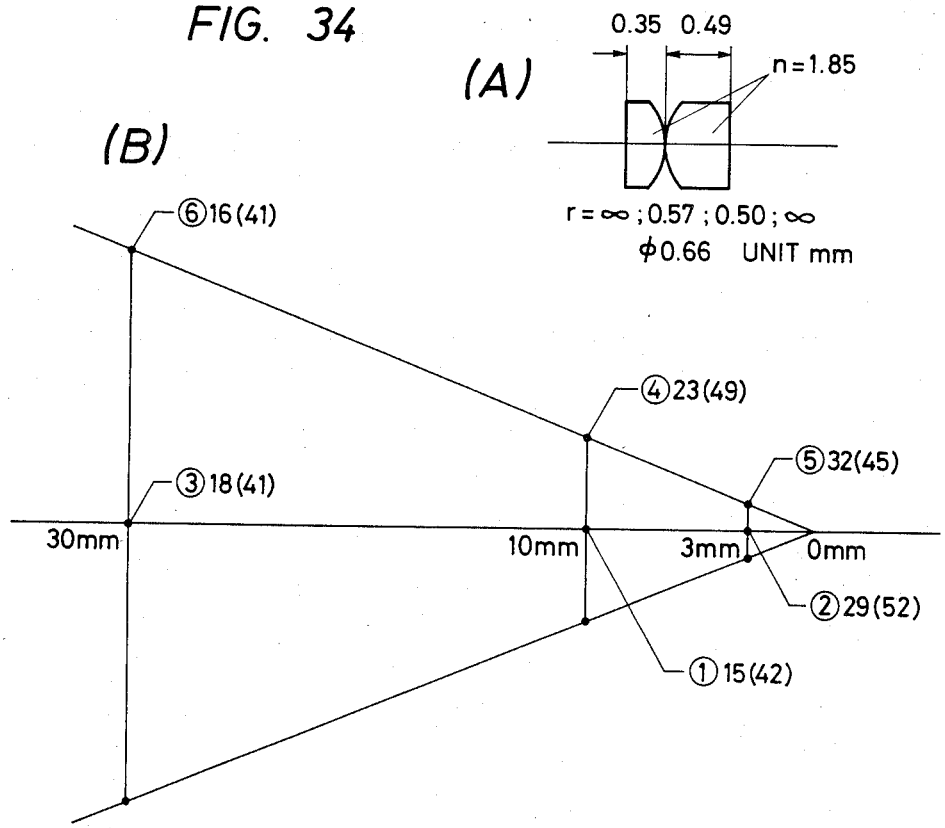
FIG. 34 is an explanatory diagram for a description of an image pickup optical system comprising two lenses.

In FIG. 34, reference numerals added with parentheses indicate spot sizes at $r_1=0.36$ mm, $r_2=0.47$ mm, lens length of 0.76 mm, $n=1.85$ and lens diameter of 0.66. These spot sizes were obtained when focused at the point 1.

Figure 35:
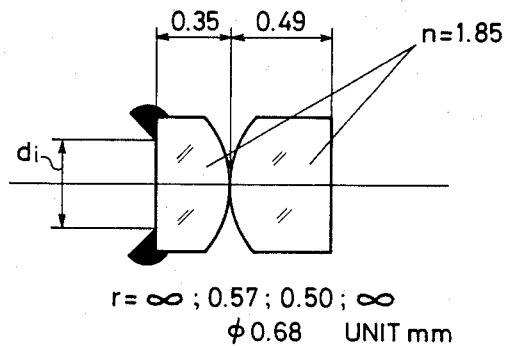
FIG. 35 is an explanatory diagram showing an image pickup optical system comprising two lenses according to the present invention.
Figure 36:
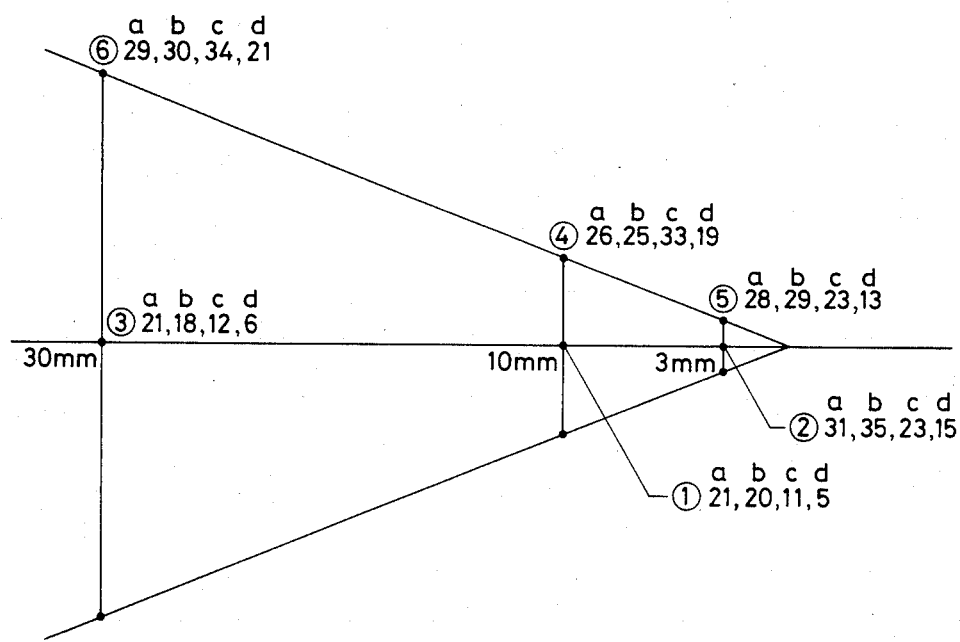
FIG. 36 is a diagram indicating a calculation of the effects which are provided when a lens iris is applied to the optical system shown in FIG. 35.
Figure 37:
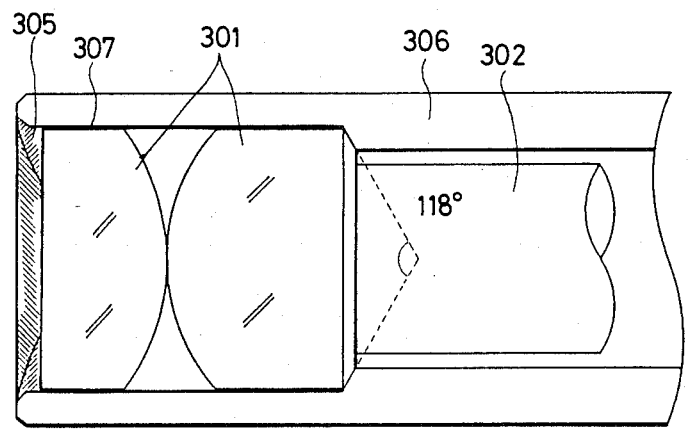
FIG. 37 is an explanatory diagram showing a concrete construction of the image pickup optical system shown in FIG. 35.
Figure 38:
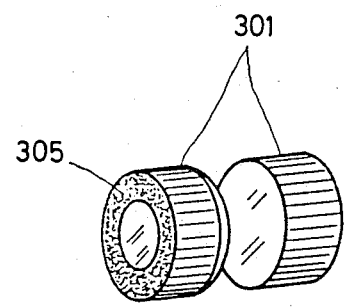
FIG. 38 is a perspective view showing the image pickup optical system which is provided with a lens stop by vacuum deposition.

FIG. 36 shows one example of an image pickup optical system comprising two convex lenses which has no lens iris. FIG. 35 shows one example of an image pickup optical system according to the invention. The spot size decreasing effect is as shown in FIG. 36. In FIG. 36, a is SP (spot size) at the front of the lens without stop. The diameter of the lens is 0.68 mm. The focal point is adjusted at point 1 (−0.010). b is SP (−0.014) at the aperture diameter of 0.60 mm. c is SP (0.011) at the aperture diameter of 0.50 mm. d is SP (0.030) at the aperture diameter of 0.40 mm (0.030). The numerals added with parentheses indicate back focus amount (mm). The unit of the spot size is μm. The view angle is 60° and diameter of image fiber is 0.47 mm. FIG. 37 shows a concrete method of combining a lens iris 305 with the optical system. In the method, a sleeve 306 is used to combine a lens 301 and an image fiber 302 together. First, the lens is fixed with cyanoacrylate adhesive, and then light shielding epoxy resin (mixed with carbon), which can protect the optical system from the entrance of water, is applied to the lens to form a lens stop thereon. FIG. 38 shows the case where a lens iris is formed on the lens by vacuum-depositing aluminum according to the masking method. As is apparent from the above description, a large mechanical lens iris for 35 mm camera lenses cannot be applied to the image pickup optical system for small diameter endoscopes.

The embodiment provides the following effects:
(1) The resolving power or the depth of field of the image pickup optical system is increased.
(2) When the method of forming the lens iris with light-shielding resin is employed, the formation of the lens iris can be achieved readily, and the aperture diameter can be quickly changed when required.
(3) When the method of forming the lens iris by vacuum deposition is employed, the aperture diameter can be provided with high accuracy.

While the invention has been described in detail and with reference to specific embodiments thereof it will be apparent to one skilled in the art that various changes and modifications can be made therein without departing from the spirit and scope of the invention.

What is claimed is:

1. A fiberscope comprising image fiber means having lens means at one end of said image fiber means for focusing an image of an object to be observed on the end of the image fiber means for transmission therethrough, said lens means having a light receiving surface for receiving light from an object, a covering tube having an end surface surrounding said image fiber means with at least a portion of said lens means protruding beyond said end surface of said tube, light guide means for transmitting light to an object extending through said tube adjacent said image fiber means and having a front end surface adjacent said end outer surface of said covering tube and a substantially solid transparent plastic body secured to the end of said fiberscope, said body covering said front end surface of said light guide means and said end surface of said tube and having a convex surface substantially flush with but not covering said light receiving surface of said lense.

2. A fiberscope as set forth in claim 1 wherein said plastic body is formed from one of epoxy resin, ultraviolet curing silicone resin, acrylic resin or urethane resin.

3. A fiberscope as set forth in claim 1 wherein liquid passage means are provided between an inner peripheral surface of said covering tube and outer peripheral surfaces of said image fiber means and said light guide means and extend through said plastic body to provide a flow of transparent liquid to flush undesirable material away of said light receiving surface of said lense means.

4. A fiberscope as set forth in claim 3 wherein said light guide means is comprised of a plurality of light guides arranged substantially symmetrically around said lens means and said liquid passage means are comprised of a plurality of liquid passages having outlet ends in the convex surface of said body and arranged in substantially symmetrical relationship with respect to said lens means.

* * * * *